(12) United States Patent
Snow et al.

(10) Patent No.: US 7,750,174 B2
(45) Date of Patent: Jul. 6, 2010

(54) FLUOROALKYL CARBINOL GENERATING SILANE SURFACE TREATMENT AGENTS

(75) Inventors: Arthur W. Snow, Alexandria, VA (US); Edward E. Foos, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 504 days.

(21) Appl. No.: 11/907,501

(22) Filed: Oct. 12, 2007

(65) Prior Publication Data
US 2008/0087197 A1   Apr. 17, 2008

Related U.S. Application Data

(60) Provisional application No. 60/851,075, filed on Oct. 12, 2006.

(51) Int. Cl.
*C07F 7/18* (2006.01)
*C07F 7/16* (2006.01)

(52) U.S. Cl. .................. 556/406; 556/465; 556/466; 556/482; 556/485

(58) Field of Classification Search .................. 556/406, 556/465, 466, 482, 485
See application file for complete search history.

(56) References Cited

U.S. PATENT DOCUMENTS 5,300,613 A * 4/1994 Kishita et al. .................. 528/26
6,001,928 A * 12/1999 Harkness et al. ............ 524/858

\* cited by examiner

*Primary Examiner*—Elvis O Price
(74) *Attorney, Agent, or Firm*—Amy L. Ressing; Stephen T. Hunnius

(57) ABSTRACT

The compound is a silane surface treatment agent and is useful for modifying the surfaces of silicon oxide and other metal oxides with hexafluorodimethyl carbinol functional groups. Additionally provided is a surface treatment procedure that effectively bonds it and other alkoxysilanes via homogeneous and heterogeneous amine catalysis onto metal oxide surfaces.

7 Claims, No Drawings

FLUOROALKYL CARBINOL GENERATING SILANE SURFACE TREATMENT AGENTS

This application claims the benefit of U.S. provisional application No. 60/851,075 filed on Oct. 12, 2006, herein incorporated by reference in its entirety.

The application is generally related to fluorinated cyclic silane coupling agents and their reaction with metal oxide surfaces to produce a high density of surface-bonded fluoroalkyl carbinol functional groups.

The use of molecular agents to treat metal oxide surfaces, particularly silicon oxide, is a long practiced art. It dates back to the 1950's when the driving application was for coupling agents to promote adhesion between glass fibers and organic resins in the development of fiber reinforced organic composites. The ability of silane coupling agents to promote better adhesion and load transfer across the glass fiber organic resin interface has been the subject of books (E. P. Plueddlemann, "Silane Coupling Agents" Plenum Press, New York, second edition (1991); K. L. Mittal (Ed.), "Silanes and Other Coupling Agents", VSP, Zeist, The Netherlands (1992) and reviews (G. Wan, F. Yan, Z. G. Teng, "The Surface Modification of Silica with APTS", in Progress in Chemistry, 18(2-3), 239 (2006); A. T. DiBenedetto, "Tailoring of Interfaces in Glass Fiber Reinforced Polymer Composites: A Review" in Materials Science and Engineering A, 302(1), 74 (2001)) and continues to be a challenge for new research. Beyond this area of fiber reinforced composite research, silane coupling agents or silanizing agents are used as surface treatment agents that confer many useful properties on surfaces such as wetting, dewetting, adhesion resistance, surface passivation and agents for nanoscale architectures among other things. The silane surface modification agent is a small molecule that typically consisted of at least two functional groups: a functionality (e.g a chlorosilane or alkoxysilane) that will anchor the molecule to a metal oxide surface and a functionality that is oriented away from the surface and interacts with the environment in which the surface is immersed. Such functionalities may be amines or carboxylic acids that can develop the acid-base properties of the surface, or siloxanes that can lower the surface friction, or photoactive groups that support various lithographies. The current application concerns the fluoroalkyl carbinol functionality, —C(RF)$_2$OH, and in particular the hexafluorodimethyl carbinol functionality, —C(CF$_3$)$_2$OH.

The fluoroalcohol functional group confers unique properties on molecular substances which qualify them for many applications. The unique properties associated with incorporation of the fluoroalcohol functional group are a strong hydrogen bonding interaction and a proton acidity coupled with a hydrophobic character. This combination of properties makes fluoroalcohol substituted compounds surface active agents in aqueous systems and as such find applications as surfactants, wetting and dispersing agents, defoamers, phase transfer agents, polymer blend formation promoters, etc. For the detection of the organophosphorous chemical warfare agents the hydrogen bonded interaction of the fluoroalcohol with the phosphoryl group is very important for the sensitivity and selectivity of point sensors in this application. Specifically, the hexafluorodimethylcarbinol group is remarkably effective in promoting chemoselective interactions with analytes such as organophosphonate esters and nitroaromatics/nitroaliphatics. For chemical sensing applications it has been incorporated into a variety of polymers (styrenes, acrylates, siloxanes, carbosilanes, etc.) which are utilized as coatings on microelectronic devices to detect trace levels of toxic compounds. The silane coupling agent approach described in this application bypasses the polymer incorporation and subsequent polymer thin film deposition by bonding to the silicon oxide (or other oxide) surface in a single step. As a small molecule applied to a surface under chemical self-assembly conditions, it provides a greater hexafluorodimethylcarbinol functional group density, and it covalently bonds a much thinner mono- or multilayer film to the SiO$_2$ surface. As such, this deposition has particularly attractive prospects for enhancing sensitivities of very high frequency (>500 MHz) SAW sensors. Its attractiveness rests in the vapor response sensitivity of the SAW sensor being dependent on the square of the frequency up to the limit where the thickness of the polymer coating deposition dampens the resonance of the SAW device. For extremely thin film deposition, this fluoroalcohol functionalizing silane agent coupled with a chemical self-assembly process has a distinct advantage over fluoroalcohol polymer depositions.

This disclosure concerns a chemistry that anticipates application for surface treatment of silicon oxide and other metal oxide surfaces. For silicon and other metal oxide surfaces the tethered fluoroalcohol functionality would impart the hydrophobic but strong hydrogen bonding character. Such a surface treatment would discourage water induced corrosion yet promote wetting and bonding. For finely divided metal oxide particulates, particularly nano-scale, a bonded monolayer of this new compound would stabilize against irreversible agglomeration as well as making such monolayer encapsulated clusters dispersible in a variety of solvents or polymer matrices. The dimensions and character of this hexafluorodimethylcarbinol terminated siloxane surface treatment are perceived to be particularly important to a chemical sensing application. In addition to the hydrogen bonded interaction with organophosphorous chemical warfare agents there is an affinity for heavily nitrated compounds such as those found in explosives. The key advantage is the ability to deposit coatings with a high hexafluorodimethylcarbinol functional group density and nanometer scale thickness such that high frequency SAW sensing devices (>500 MHz) can take advantage of a sensitivity enhancement which increases with the square of the frequency without having the resonance damped out by an inability to deposit coatings of controlled nanometer thicknesses.

This application comprises a series of compounds illustrated by the general formula:

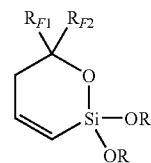

Where:
R = alkyl group
R$_{F1}$ = fluoroalkyl group
R$_{F2}$ = fluoroalkyl group and the method by which this compound can be made to react with a metal oxide surface to produce a structure that bonds with oxygen atoms in the metal oxide surface and that forms a fluoroalkyl carbinol functional group comprised by the general formula below:

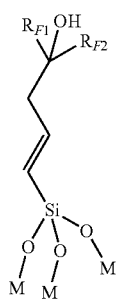

Where:
$R_{F1}$ = fluoroalkyl group
$R_{F2}$ = fluoroalkyl group
M = metal atoms of the metal oxide surface This application further comprises a composition of matter comprising the metal oxide surface having the group $O_3SiCH=CHCH_2CR_{F1}R_{F2}OH$ where the three oxygen atoms attached to the silicon are in common with the metal oxide surface, $R_{F1}$ and $R_{F2}$ are fluoroalkyl groups which may also comprise heteroatoms and M may be Si, Al or Ti.

The disclosure can be illustrated by the example depicted below:

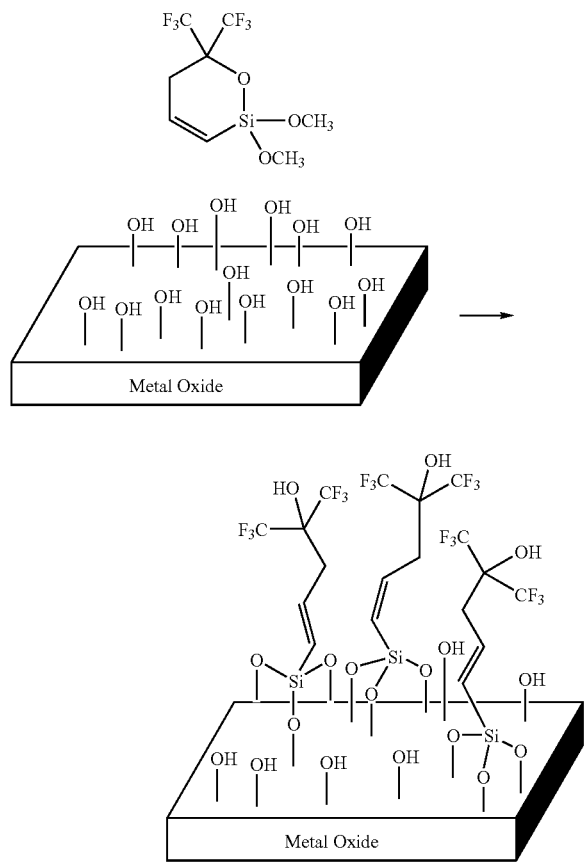

The example compound is prepared from the electrophilic reaction of hexafluoroacetone with the terminal olefin of allyltrimethoxysilane as depicted below.

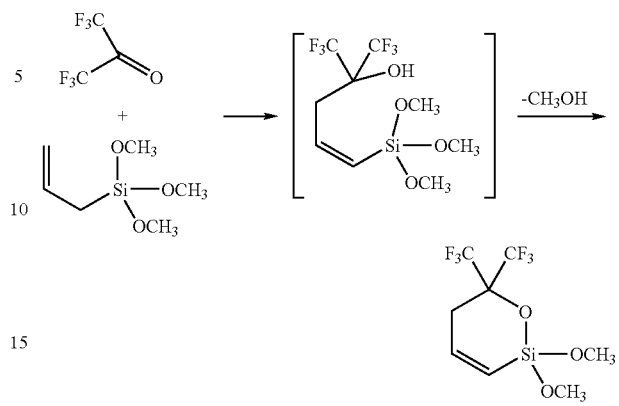

The intermediate in brackets was initially expected to be the product, but the tertiary hydroxyl group derived from the hexafluoroacetone is well-situated to nucleophilically displace one of the methoxy groups on the silicon to eliminate methanol and close the six membered ring. The synthesis, purification and characterization of this compound are described in detail in Example 1. The ring closure from the intermediate to product is perceived as advantageous as the product is more hydrolytically stable making it easier to store, more volatile making it easier to purify and to handle as a vapor and of higher symmetry making the structural characterization easier to interpret. The reaction chemistry between fluoroalkyl ketones and terminal olefins is general and many different combinations of fluoroalkyl ketone and allyltrialkoxysilane reagents can be employed. The preferred reagents are hexafluoroacetone and allyltrimethoxysilane and allyltriethoxy silane because these are readily available materials and yield a product in high yield. These products have attractive characteristics of facile purification, physical handling and analytical diagnostics along with good chemical stability for storage and controllable reactivity for surface modification. Other ketone reagents would include perfluorobutanone, the various isomeric perfluorinated pentanones, hexanones, heptanones and higher analogues. Other allyltrialkoxysilanes would include the allyltripropoxy-, allyltributoxy-, allyltripentoxy- and higher trialkoxy-analogues of this reagent. Alkoxy substituents of mixed chain lengths as well as branched chains are also practicable.

This series of compounds acts as a metal oxide surface treatment agent by hydrolyzing the three Si—O—C bonds. One Si—O—C bond opens the ring to regenerate the hexafluorodimethylcarbinol group and a silanol group. The other two Si—O—C bonds are directly hydrolyzed to silanol groups. This is followed by a condensation of silanol groups to form Si—O-M bonds where M is Si, Al or Ti. Both reactions require acid or base catalysis. In the reaction below a homogeneous model compound system was run to confirm the structures in this chemical transformation.

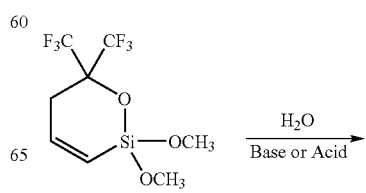

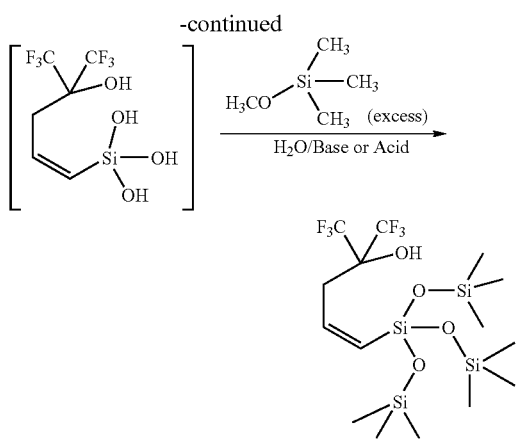

This model compound product structural characterization includes spectroscopy (MS, IR, $^1$H, $^{13}$C, $^{19}$F and $^{31}$Si NMR) and elemental analyses to confirm its structure. The replacement of the hydrolytically sensitive Si—O—C bonds by the much more stable Si—O—Si bonds is the driving force for this reaction. In a heterogeneous system where a $SiO_2$ substrate is involved, its silanol functional groups are reactive sites for bonding the silanizing agent and its polymer to the $SiO_2$ surface. If the surface is not sufficiently acidic or basic along with some adsorbed water the reaction does not proceed as written. This transformation is depicted below.

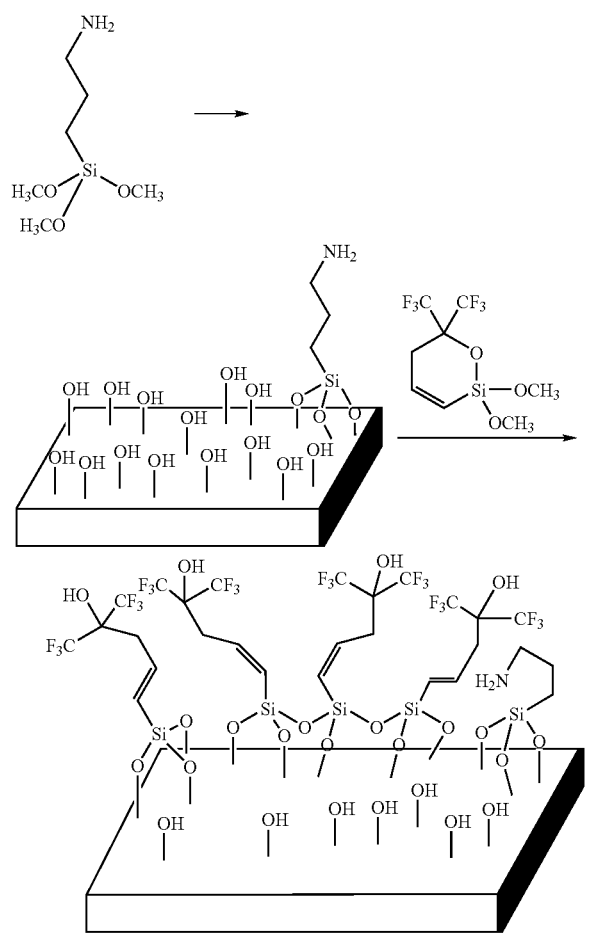

Most metal oxides are amphoteric and do have a trace of strongly adsorbed residual water. A lower level of reactivity can be observed can be observed without purposefully added water and catalytic acid or basic moieties. This is demonstrated in Examples 2 and 3. The level of reactivity correlates with the surface density of the fluoroalkyl carbinol functional groups bonded to the metal oxide surface and is measured by the fluorine:silicon (F:Si) ratio of elemental composition in the x-ray photoelectron spectrum (XPS). In Example 2, a silicon oxide substrate has been treated with a solution of the fluoroalkyl silanizing agent (designated by the acronym FSA) synthesized in Example 1 without purposefully added water or catalytic entities, and a modest F:Si ratio of 0.10 is measured indicating a low level of surface bonding has occurred. In Example 3, water is added to the FSA solution into which the $SiO_2$ substrate is immersed, and only a nominal increase in the F:Si (0.11) ratio results. When strong acid catalysts, such as p-toluenesulfonic acid, are added to the FSA-water treatment solution, the solution immediately turns cloudy indicating the FSA is rapidly polymerizing with the polymer phase separating from the chloroform solution. This is not desirable as the intent is that the FSA react preferentially with the metal oxide surface. When basic catalysts, such as n-butylamine, are added to the FSA-water treatment solution, the solution remains clear for several hours indicating that the polymerization, if it is occurring, is not near as rapid as with the acid catalyst. When the $SiO_2$ substrate is immersed in the FSA-water-butylamine treatment solution as shown in Example 4, a significant increase in the F:Si (0.18) ratio occurs. When an amine-functionalized silanizing agent, 3-aminopropyltrimethoxy silane (designated by the acronym APS) that has the capability of bonding itself to the metal oxide surface is used in place of butylamine as in Example 5, a modest increase in the F:Si (0.19) is observed. Examples 4 and 5 are examples of homogeneous catalysis. Pre-bonding the amine functionality to the metal oxide surface prior to exposure to the FSA-water treatment solution is a heterogeneous catalysis and makes the surface treatment more efficient. In Examples 6 and 7, the APS is pre-bonded to the $SiO_2$ substrate surface by treatment with APS-water chloroform solutions with the APS-water concentrations at respective low and high levels. The XPS measurement of the nitrogen:silicon (N:Si) ratios correlates with the concentration differences in the APS-water treatment solutions. In the scope of this disclosure the amine is considered to be a catalyst in that it is not consumed during the reaction during reaction of the fluoroalkyl silanizing agent with the metal oxide surface, and the expression catalytic quantity is considered to mean that the relative molar quantity employed is less than stoichiometric to the fluoroalkyl silanizing agent. In Example 8, the $SiO_2$ substrate with the pre-bonded APS from Example 6 is treated with the FSA-water solution and displays a significantly enhanced F:Si (0.37) for the heterogeneous catalysis compared with the F:Si (0.19) for the analogous experiment of Example 5 with homogeneous catalysis. Example 9 shows that doubling the time for exposure to the FSA-water treatment solution results in a modest increase of F:Si (0.43) from that of Example 8 with F:Si (0.37). Example 10 employs the $SiO_2$ substrate with the higher density pre-bonded APS from Example 7, and treatment of this substrate with the FSA-water solution displays a marked increase in density of surface bonded FSA as reflected by the F:Si (0.82). Example 11 shows the effect of changing the solvent of the FSA-water treatment solution from chloroform to 2-propanol for an experiment analogous to that in Example 10. This change caused the F:Si to drop from 0.82 to 0.25. In Example 12, the conditions of the experiment in Example 11 are replicated except the concentration of FSA and water in the FSA-water treatment solution are tripled, and this causes the F:Si to increase from 0.25 to 0.42. In Example 13, the metal oxide substrate is changed to aluminum oxide, and the FSA-water treatment exposure conditions of Example 12 are replicated. The F:Al is 0.52 indicating that a significant amount of the FSA bonds to the aluminum oxide. In Example 14, the FSA is deposited from the vapor phase onto the APS pre-bonded substrate of Example 7 instead of from solution to demonstrate that a vapor deposition reaction is also a workable method.

Having been described, the following examples are given to illustrate specific applications. These specific examples are not intended to limit the scope described in this application.

EXAMPLE 1

Synthesis of 1,1-dimethoxy-1-sila-5,5-(bistrifluoromethyl)-6-oxycyclohex-2-ene (Fluoroalkyl Silanizing Agent, FSA). This procedure is derived from chemistry involving the electrophilic addition of a perfluoroketone to a terminal olefin. To a 50 ml Fisher-Porter reactor fitted with a magnetic stirring bar and flushed with dry nitrogen were pipetted 10.00 ml (59.2 mmol) allyltrimethoxysilane. Under positive pressure of dry nitrogen, the Fisher-Porter reactor was connected to a lecture bottle of hexafluoroacetone through a "T" in the nitrogen purge line and cooled to −78 C. Hexafluoroacetone (11.76 g, 70.8 mmol) was condensed in the Fisher-Porter reactor while monitoring the mass of the lecture bottle. The inlet to the Fisher-Porter reactor was removed under positive nitrogen pressure, and the reactor was sealed with a pressure cap behind a blast shield. On warming to room temperature the allyltrimethoxysilane and hexafluoroacetone were observed to be immiscible liquids that form a cloudy suspension when rapidly stirred. The reaction was run at 23 C for 24 hr. During the initial hour a mild exotherm was observed, and after 3 hr, the reaction mixture was observed to become uniphase. On opening the Fisher-Porter reactor, the excess hexafluoroacetone boiled off leaving a colorless liquid. This liquid was distilled at reduced pressure through a 30 cm heated column to yield a center cut fraction (67-71° C. at 4 torr) of 14.28 g (81.5%). This compound hydrolyzes slowly on contact with water and should be stored refrigerated and well-protected from atmospheric moisture. $^1$H NMR (CDCl$_3$): 2.76 (d, 2H, CH$_2$), 3.58 (s, 6H, O—CH$_3$), 5.77 (d of t, 1H, =CH—Si), 6.81 (d of t, 1H, CH$_2$CH=CH); $^{13}$C NMR: 27.4 (CH$_2$), 50.5 (OCH$_3$), 78.6 (septet, CH$_2$C(CF$_3$)$_2$O), 119.9 (=CH—Si), 123 (quartet, CF$_3$), 146.6 (CH$_2$CH=CH); $^{19}$F NMR: −78.99; $^{29}$Si NMR: −62.97; M$^+$/e, 296.

EXAMPLE 2

Uncatalyzed Anhydrous FSA Treatment of SiO$_2$ Surface. The substrate is a silicon wafer with a thermally deposited 100 nm film of SiO$_2$. Immediately before the FSA surface treatment, it was subjected to a Standard Cleaning No. 1 (SC1) procedure which involved a 10 min immersion in a 1:1:3 volume ratio mixture of concentrated (30%) hydrogen peroxide: concentrated (30%) ammonium hydroxide: triple distilled water at 100° C. followed by a double wash with triple distilled water and blown dry with high purity nitrogen. A surface treatment solution of 0.033 M FSA in CHCl$_3$ was prepared. The freshly cleaned substrate was immersed in the surface treatment solution for a 1 hr reaction time after which it was washed twice with high purity CHCl$_3$ and blown dry with high purity nitrogen. The quantity of FSA bonded to the substrate surface was analyzed by x-ray photoelectron spectroscopy (XPS) as the fluorine:silicon (F:Si) elemental composition ratio. found F:Si=0.10

EXAMPLE 3

Uncatalyzed Hydrated FSA Treatment of SiO$_2$ Surface. The procedure in Example 2 was followed with the exception that the surface treatment solution was composed of two solutes: 0.033 M FSA and 0.017 M H$_2$O both in CHCl$_3$. F:Si=0.11

EXAMPLE 4

Butylamine Catalyzed and Hydrated FSA Treatment of SiO$_2$ Surface. The procedure in Example 2 was followed with the exception that the surface treatment solution was composed of three solutes: 0.003 M n-butylamine, 0.033 M FSA and 0.017 M H$_2$O all in CHCl$_3$. F:Si=0.18

EXAMPLE 5

3-Aminopropyltrimethoxysilane (APS) Homogeneously Catalyzed and Hydrated FSA Treatment of SiO$_2$ Surface. The procedure in Example 2 was followed with the exception that the surface treatment solution was composed of three solutes: 0.003 M APS, 0.033 M FSA and 0.017 M H$_2$O all in CHCl$_3$. F:Si=0.19

EXAMPLE 6

Immobilization of APS on SiO$_2$ Surface for Heterogeneous Catalysis. A SiO2 substrate was SC1 cleaned as described in Example 2 then immersed in a solution composed of two solutes, 0.003 M APS and 0.003 M H$_2$O both in CHCl$_3$ for 2 hr followed by washing twice with high purity CHCl$_3$ and blown dry with high purity nitrogen. The quantity of APS bonded to the substrate surface was analyzed by XPS as the nitrogen:silicon (N:Si) elemental composition ratio. found N:Si=0.18

EXAMPLE 7

Immobilization of APS (High Concentration) on SiO$_2$ Surface for Heterogeneous Catalysis. The procedure in Example 6 was followed with the exception that the surface treatment solution was composed of higher solute concentrations: 0.008 M APS and 0.008 M H$_2$O both in CHCl$_3$. N:Si=0.37

EXAMPLE 8

3-Aminopropyltrimethoxysilane (APS) Heterogeneously Catalyzed and Hydrated FSA Treatment of SiO$_2$ Surface. The APS treated substrate of Example 6 was immersed in a surface treatment solution composed of two solutes: 0.033 M FSA and 0.017 M H$_2$O both in CHCl$_3$ for 1 hr followed by washing twice with high purity CHCl$_3$ and blowing dry with high purity nitrogen. The quantity of FSA bonded to the substrate was analyzed by XPS. Found: F:Si=0.38

EXAMPLE 9

3-Aminopropyltrimethoxysilane (APS) Heterogeneously Catalyzed and Hydrated FSA Treatment of SiO$_2$ Surface. The procedure of Example 8 was followed with the exception that the immersion time for reaction of the FSA with the heterogeneously catalyzed substrate was increased to 2 hr. F:Si=0.43

EXAMPLE 10

3-Aminopropyltrimethoxysilane (APS) Heterogeneously Catalyzed and Hydrated FSA Treatment of $SiO_2$ Surface. The APS treated substrate of Example 7 was immersed in a surface treatment solution composed of two solutes: 0.10 M FSA and 0.05 M $H_2O$ both in $CHCl_3$ for 1.5 hr followed by washing twice with high purity $CHCl_3$ and blowing dry with high purity nitrogen. The quantity of FSA bonded to the substrate was analyzed by XPS. Found: F:Si=0.82

EXAMPLE 11

3-Aminopropyltrimethoxysilane (APS) Heterogeneously Catalyzed and Hydrated FSA Treatment of $SiO_2$ Surface. The APS treated substrate of Example 7 was immersed in a surface treatment solution composed of two solutes: 0.10 M FSA and 0.05 M $H_2O$ both in 2-propanol for 2 hr followed by washing twice with high purity 2-propanol and blowing dry with high purity nitrogen. The quantity of FSA bonded to the substrate was analyzed by XPS. Found: F:Si=0.25

EXAMPLE 12

3-Aminopropyltrimethoxysilane (APS) Heterogeneously Catalyzed and Hydrated FSA Treatment of $SiO_2$ Surface. The APS treated substrate of Example 7 was immersed in a surface treatment solution composed of two solutes: 0.30 M FSA and 0.15 M $H_2O$ both in 2-propanol for 2 hr followed by washing twice with high purity 2-propanol and blowing dry with high purity nitrogen. The quantity of FSA bonded to the substrate was analyzed by XPS. Found: F:Si=0.42

EXAMPLE 13

3-Aminopropyltrimethoxysilane (APS) Heterogeneously Catalyzed and Hydrated FSA Treatment of $Al_2O_3$ Surface. The substrate is a thin aluminum disc with a native oxide deposited on the surface. This substrate was cleaned immediately before APS catalyst immobilization by a 10 min immersion in concentrated sulfuric acid followed by washing twice with triple distilled water and blowing dry with high purity nitrogen. The APS catalyst immobilization was conducted following the procedure of Example 7. This substrate was then immersed in a surface treatment solution composed of two solutes: 0.10 M FSA and 0.05 M $H_2O$ both in $CHCl_3$ for 1.5 hr followed by washing twice with high purity $CHCl_3$ and blowing dry with high purity nitrogen. The quantity of FSA bonded to the substrate was analyzed by XPS as the F:Al elemental composition ratio. Found: F:Si=0.52

EXAMPLE 14

FSA Vapor Treatment of SiO2 Surface Activated by Immobilization of APS Catalyst. The APS treated substrate of Example 7 was placed in an evacuated chamber into which was flooded the vapor of FSA at a concentration corresponding to its 23° C. vapor pressure (~0.3 torr). The substrate in the FSA vapor was heated at 130° C. for 1 hr. The quantity of FSA bonded to the substrate was analyzed by XPS. Found: F:Si=0.075.

Obviously, many modifications and variations of the present are possible in light of the above teachings. It is therefore to be understood that the claimed may be practiced otherwise than as specifically described. Any reference to claim elements in the singular, e.g., using the articles "a," "an," "the," or "said" is not construed as limiting the element to the singular.

What is claimed is:

1. A compound comprising the formula:

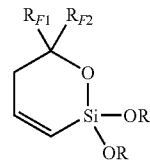

Where:
R = alkyl group
$R_{F1}$ = fluoroalkyl group
$R_{F2}$ = fluoroalkyl group wherein $R_{F1}$ and $R_{F2}$ are independently selected from substituted or unsubstituted perfluoroalkyl groups and R1 and R2 are a hydrocarbon alkyl group.

2. The compound of claim 1 wherein $R_{F1}$ is $F_3C_n(F_2C)$ and $R_{F2}$ is $(C_{F2})_mC_{F3}$ and $R_1$ is $(CH_2)_xCH_3$ and $R_2$ is $(CH_2)_yCH_3$ and can be represented by the structure:

and wherein m and n are independently selected from values of 0, 1 and 2, and x and y are independently selected from values of 0 and 1.

3. The compound of claim 1, wherein the compound has the formula:

4. The compound of claim 1, wherein the compound has the formula:

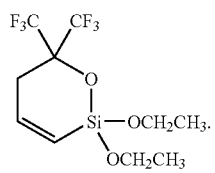

5. A method of making a compound comprising the formula

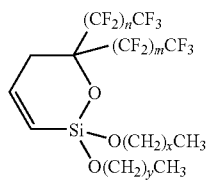

comprising:
reacting a perfluoroketone having the formula $CF_3(CF_2)_n$ $CO(CF_2)_mCF_3$ with an allyltrialkoxysilane having the formula $CH_2$=$CHCH_2Si(O(CH_2)_xCH_3)_3$ wherein n and m are independently selected from values of 0, 1, 2, 3, 4, 5, and 6 and x is selected from values of 0 and 1.

6. The method according to claim 5 wherein the perfluoroketone is hexafluoroacetone and wherein the allyltrialkoxysilane is allyltrimethoxysilane and the compound is represented by the formula:
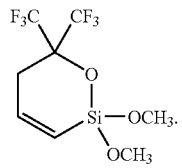
7. A method of making the compound of claim 5, wherein the compound has the formula:
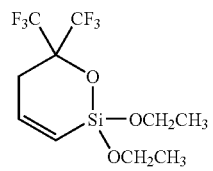
comprising
reacting hexafluoroacetone with allyltriethoxysilane.
* * * * *